United States Patent [19]

Fontanelli

[11] Patent Number: 5,575,994
[45] Date of Patent: Nov. 19, 1996

[54] DERMATOLOGICAL AND COSMETIC COMPOSITIONS

[75] Inventor: Luciano Fontanelli, Pisa, Italy

[73] Assignee: Istituto Gentili S.p.A., Pisa, Italy

[21] Appl. No.: 244,147

[22] PCT Filed: Nov. 12, 1992

[86] PCT No.: PCT/EP92/02597

§ 371 Date: May 18, 1994

§ 102(e) Date: May 18, 1994

[87] PCT Pub. No.: WO93/09760

PCT Pub. Date: May 27, 1993

[30] Foreign Application Priority Data

Nov. 22, 1991 [IT] Italy ................... MI91A3127

[51] Int. Cl.$^6$ .................. A61K 7/00; A61K 7/48; A61K 7/06
[52] U.S. Cl. .............. 424/78.03; 514/844; 514/847
[58] Field of Search .............. 424/78.03; 514/844, 514/847

[56] References Cited

U.S. PATENT DOCUMENTS 4,883,792  11/1990  Timmins et al. ................... 514/169

FOREIGN PATENT DOCUMENTS 2538  3/1991  WIPO.

OTHER PUBLICATIONS

CA 107:102711 1987.
CA 114:192632 1990.
CA 77:39054 1971.
CA 115:214871 1991.

*Primary Examiner*—Paul J. Killos
*Attorney, Agent, or Firm*—Bucknam and Archer

[57] ABSTRACT

Dermatological and cosmetic compositions having high endermicity and antiageing activity and high stability are herein described consisting of: 1) emulsifying and self-emulsifying agents, having o/w activity formed by a mixture containing (as % w/w); 1') polyethylene glycol mono- or distearate 0.5–5.0%; 2') polyglycol esters of saturated or unsaturated $C_{14}$–$C_{20}$ fatty acids 1.0–10.0%; 3') cetyl alcohol and optionally other higher alcohols, comprising free or esterified sterols 1.0'16.0%; 2) sodium versenate and anti-oxidant agents 0.1–5.0%; 3) anti-mould and bacteriostatic agents 0.05–0.1%; 4) active ingredients 1–30%; 5) purified water F.U. q.s. to 100%.

10 Claims, No Drawings

DERMATOLOGICAL AND COSMETIC COMPOSITIONS

This application is a 371 of PCT/EP92/02597 filed Nov. 12, 1992.

The present invention relates to dermatological and cosmetic compositions and particularly to compositions having antiageing activity; said compositions are also useful in the treatment of burns, wounds and are characterized by a high stability such as to make them also suitable for the stabilization of active ingredients.

Skin is formed by cells the state of which affects the external appearance of epidermis. Skin ageing derives from a slowing of the derm functions, particularly nutrition, respiration, hydration, regeneration and cutaneous tissues protection. Skin ageing is a natural phenomenon the causes of which are of different origin and can be more or less fast for each person. Generally, the function slowing of certain cells, the role of which is very important in maintaining the integrity of derm structure, begins around one's thirties. This phenomenon may begin at a more or less early age, due to many factors, such as genetic set, general health state, each individual's peculiar way of life.

The object of the present invention is to provide dermatological and cosmetic compositions having antiageing activity and having high stability, also in the presence of active ingredients of various kind.

The compositions according to the invention consist of:

| | |
|---|---|
| 1) emulsifying and self-emulsifying agents, having o/w activity formed by a mixture containing (as % w/w) | |
| 1') polyethylene glycol mono- or distearate | 0.5–5.0% |
| 2') polyglycol esters of saturated or unsaturated $C_{14}$–$C_{20}$ fatty acids | 1.0–10.0% |
| 3') cetyl alcohol and optionally other higher alcohols, comprising free or esterified sterols | 1.0–16.0% |
| 2) sodium versenate and antioxidant agents | 0.1–5.0% |
| 3) anti-mould and bacteriostatic agents | 0.05–0.1% |
| 4) active ingredients having derm reconstituting activity | 1–30% |
| 5) purified water F.U. | q.s. to 100% |

Polyethylene glycols, having various molecular weight, weight, for example ranging from 200 to 10,000, preferably from 400 to 2,000, more preferably 1,000, can be used. Polyethylene glycol 1,000 monostearate is particularly preferred.

The antioxidant agents are selected from the group consisting of:

a) polyunsaturated fatty acids, preferably belonging to vitamin F group;

b) tocopheryl derivatives, preferably tocopheryl acetate.

Examples of anti-mould and/or bacteriostatic agents are methyl or propyl p-oxybenzoates.

The active ingredients preferably have derm reconstituting activity. Examples of said active ingredients, which can be used alone or combined each other, are collagen, in the several forms thereof, esurosamine, elastin, amino acids, peptides, mucopolysaccharides.

The compositions of the invention are characterized by a remarkable eudermicity, therefore, they act in an extraordinarily favourable extent on skin stretching and smoothness (anti-wrinkle effect), translucency, on tissue stiffening, turgidity and elasticity, on the reduction of irregular fat accumulation in subcutaneous connective ("cellulitis"). The same favourable effects are exerted by the compositions on skin irritations on children, due to wet linens or sweat, on feet irritations due to maceration, on sun-induced irritations.

Further, the compositions of the invention also carry out a surprising dermatological activity on burns, crural ulcer, wound healings, bedsores, accelerating their recovery.

A particular and surprising aspect of the present invention lies in the fact that the above mentioned compositions, with a formulation excluding the active ingredients of the above point 4, act as stabilizing carriers towards several active ingredients, such as vitamins, hormones, antibiotics. Accordingly, said compositions are useful for the preparation of pharmaceutical compositions containing active ingredients, which are subject to degradation due to environmental conditions (temperature, humidity, oxidants, etc.).

Several stability tests, through chromatographic analysis, established that the compositions of the invention maintain the titre of the active ingredients therein enclosed within the limits fixed at room temperature; particularly some vitamins showed a titre loss not higher then 10% within two years.

The compositions of the invention are prepared according to the techniques which are well-known in dermatology and cosmetics, said compositions may be in the form of creams, lotions, milks, ointments, oils, ampoules, masks, gels, pads, sprays.

According to one of the advantageous embodiments of the invention, both creams and milks can be prepared with the same components.

Tolerability tests, carried out on dermatological and cosmetic compositions of the present invention, proved that said compositions are perfectly tolerated and cause no irritations, thus confirming their high eudermicity.

The following examples further illustrate the invention.

EXAMPLE 1

To prepare 100 g of "base" cream:

| | |
|---|---|
| Purified water | 43.220 g |
| Hamamelis water | 27.500 g |
| Cetyl alcohol | 16.000 g |
| Free and esterified sterols | 1.000 g |
| Methyl p-oxybenzoate | 0.150 g |
| Polyethylene glycol 1,000 monostearate | 3.000 g |
| Propyl p-oxybenzoate | 0.050 g |
| Propyl gallate | 0.030 g |
| Propylene glycol | 7.000 g |
| Rose essence | 0.250 g |
| Disodiun versenate | 0.050 g |
| Vitamin F 80% | 1.250 g |
| Polyglycol esters of saturated or unsaturated $C_{14}$–$C_{20}$ fatty acids | 0.500 g |

EXAMPLE 2

To prepare 100 g of Elastin cream:

| | |
|---|---|
| Elastin (anhydrous) | 1–2 g |
| Linol-linoleic acid | 1.25 g |
| Cetyl alcohol | 12.00 g |
| Polyethylene glycol 1,000 monostearate | 2.25 g |
| Polyglycol esters of saturated or unsaturated $C_{14}$–$C_{20}$ fatty acids | 0.375–0.75 g |
| Free and esterified sterols | 0.75 g |
| Methyl p-oxybenzoate | 0.13 g |
| Propyl p-oxybenzoate | 0.07 g |
| Propyl gallate | 0.30 g |
| Versenic acid sodium salt | 0.05 g |
| Hamamelis water | 20.50 g |
| Propylene glycol | 5.25 g |
| Purified water | 55.975–54.600 g |
| Rose essence | 0.20 g. |

EXAMPLE 3

To prepare 100 g of Collagen cream:

| | |
|---|---|
| Soluble collagen (anhydrous)) | 1.20 g |
| Vitamin F (polyunsaturated fatty acid) | 1.15 g |
| Elastin | 0.50 g |
| Esurosamine | 0.50 g |
| Vitamin E (Tocopheryl acetate) | 0.20 g |
| Cetyl alcohol | 7.50 g |
| Polyethylene glycol 1,000 monostearate | 3.00 g |
| Polyglycol esters of saturated or unsaturated fatty acids | 1.50 g |
| Free and esterified sterols | 1.50 g |
| Methyl p-oxybenzoate | 0.10 g |
| Propyl p-oxybenzoate | 0.01 g |
| Propyl gallate | 0.02 g |
| Versenic acid sodium salt | 0.05 g |
| PCV-1845/2 Givaudan essence | 0.30 g |
| Purified water | 82.47 g. |

EXAMPLE 4

To prepare 100 g of detergent milk:

| | |
|---|---|
| Purified water | 45.050 g |
| Hamamelis water | 27.500 g |
| Cetyl alcohol | 2.500 g |
| Free and esterified sterols | 1.000 g |
| Polyglycol esters of saturated or unsaturated $C_{14}$–$C_{20}$ fatty acids | 5.000 g |
| Elastin | 1.000 g |
| Esurosamine | 1.000 g |
| Methyl p-oxybenzoate | 0.130 g |
| Polyethylene glycol 1,000 monostearate | 0.750 g |
| Propyl p-oxybenzoate | 0.070 g |
| Propyl gallate | 0.300 g |
| Propylene glycol | 14.000 g |
| PCV-1845/2 Givaudan essence | 0.200 g |
| Versenic acid sodium salt | 0.050 g |
| Vitamin F 80% | 1.250 g |
| Vitamin E (Tocopheryl-acetate) | 0.200 g. |

I claim:

1. A dermatological and cosmetic composition consisting of the following:

an emulsifying and self-emulsifying agent, having o/w activity formed by a mixture containing (as % w/w)

| | |
|---|---|
| 1') a polyethylene glycol mono- or distearate | 0.5–5.0%; |
| 2') a polyglycol ester of a saturated or unsaturated $C_{14}$–$C_{20}$ fatty acid | 1.0–10.0%; |
| 3') cetyl alcohol and 0.75–1.50% of free or esterified sterols | 1.0–16.0%; |
| 2) sodium versenate and an antioxidant agent | 0.1–5.0%; |
| 3) an anti-mold and bacteriostatic agent | 0.05–0.1%; |
| 4) an active ingredient having anti-wrinkle effect | 1–30%; |
| 5) purified water F.U. | q.s. to 100%. |

2. The composition according to claim 1, wherein said antioxidant agent 2) is a member selected from the group consisting of polyunsaturated fatty acids, and tocopherol derivatives, said active ingredient component 4) is a member selected from the group consisting of collagen, esurosamine, elastin, amino acids, peptides, mucopolysaccharides and mixtures thereof.

3. The composition according to claim 1, wherein said active ingredient 4) is a member selected from the group consisting of vitamins, hormones and antibiotics.

4. The composition according to claim 1, wherein said agent 1') is polyethylene glycol monostearate wherein polyethylene glycol has molecular weight of 1000.

5. The composition according to claim 2, wherein said antioxidant agent is tocopheryl acetate.

6. The composition according to claim 1, wherein said agent 3) is methyl or propyl p-oxybenzoate.

7. The composition according to claim 1, in the form of a milk, a lotion, a cream, an ointment, an oil, an ampoule, a mask, a gel, a pad, or a spray.

8. A dermatological and cosmetic composition consisting of the following:

| | |
|---|---|
| 1) an emulsifying and self-emulsifying agent, having o/w activity formed by a mixture containing (as % w/w) | |
| 1') a polyethylene glycol mono- or distearate | 0.5–5.0%; |
| 2') a polyglycol ester of a saturated or unsaturated $C_{14}$–$C_{20}$ fatty acid | 1.0–10.0%; |
| 3') cetyl alcohol | 1.0–16.0%; |
| 2) sodium versenate and an antioxidant agent | 0.05–0.1%; |
| 3) an anti-mold and bacteriostatic agent | 0.05–0.1%; |
| 4) an active ingredient having anti-wrinkle effect | 1–30%; |
| 5) purified water F.U. | q.s. to 100%. |

9. The composition according to claim 8 wherein said active ingredient is elastin, esurosamine or mixtures thereof.

10. The composition according to claim 8 wherein said antioxidant is tocopheryl acetate.

* * * * *